US010834357B2

(12) United States Patent
Saini et al.

(10) Patent No.: US 10,834,357 B2
(45) Date of Patent: Nov. 10, 2020

(54) CONTINUOUS VIDEO CAPTURE GLASSES (71) Applicant: HINDSIGHT TECHNOLOGIES, LLC, Los Angeles, CA (US)

(72) Inventors: Armaan Saini, La Palma, CA (US); Casey Spencer, Woodland Hills, CA (US); Vivek Vinodh, Los Angeles, CA (US)

(73) Assignee: HINDSIGHT TECHNOLOGIES, LLC

( * ) Notice: Subject to any disclaimer, the term of this patent is extended or adjusted under 35 U.S.C. 154(b) by 13 days.

(21) Appl. No.: 16/293,462

(22) Filed: Mar. 5, 2019

(65) Prior Publication Data
US 2019/0273888 A1    Sep. 5, 2019

Related U.S. Application Data (60) Provisional application No. 62/638,820, filed on Mar. 5, 2018.

(51) Int. Cl.
*H04N 5/77* (2006.01)
*G02B 27/01* (2006.01)
*G06F 3/01* (2006.01)
*H04N 5/232* (2006.01)

(52) U.S. Cl.
CPC ............ *H04N 5/772* (2013.01); *G02B 27/017* (2013.01); *G06F 3/013* (2013.01); *H04N 5/23248* (2013.01); *G02B 2027/0178* (2013.01); *G02B 2027/0187* (2013.01)

(58) Field of Classification Search
None
See application file for complete search history.

(56) References Cited

U.S. PATENT DOCUMENTS

| 5,140,436 A | 8/1992 | Blessinger |
| 7,088,387 B1 | 8/2006 | Freeman et al. |
| 8,310,540 B2 | 11/2012 | DeKeyser |
| (Continued) | | |

FOREIGN PATENT DOCUMENTS

| WO | WO2016012865 A2 | 1/2016 |
| WO | WO2017212958 A1 | 12/2017 |

OTHER PUBLICATIONS

Casey Newton, Here's how Snapchat's new Spectacles will work, The Verge, Sep. 24, 2016.
PogoTec Introduces PogoLoop, BusinessWire, Mar. 31, 2017.

*Primary Examiner* — Eileen M Adams
(74) *Attorney, Agent, or Firm* — Gary L. Eastman; Eastman McCartney Dallmann LLP (57) ABSTRACT

A set of glasses frames includes electronic components for video capture and is configured to continuously capture video in a twenty-second loop. On the frames is a capture button that, when pressed, causes the electronic circuitry to store the prior twenty seconds and the following twenty seconds, for a total of forty seconds of video in non-transitory memory. The electronic circuitry in the frames also includes a Bluetooth radio and a Wi-Fi radio, enabling the frames to communicate with a mobile device, and more particularly to provide the saved twenty-second video clips to an app running on the mobile device. The app allows for storage of the video clips on the phone, editing of the video clips, upload of the video clips to the Internet, and configuring user-adjustable settings on the electronic circuitry of the glasses.

8 Claims, 6 Drawing Sheets (56) References Cited

U.S. PATENT DOCUMENTS

| | | |
|---|---|---|
| 8,928,752 B2 | 1/2015 | DeKeyser |
| 9,978,372 B2 | 5/2018 | Örthagen et al. |
| 2003/0020950 A1 | 1/2003 | Hunter |
| 2009/0051768 A1 | 2/2009 | DeKeyser |
| 2015/0003819 A1 | 1/2015 | Ackerman |
| 2015/0139605 A1 | 5/2015 | Wiklof |
| 2016/0190859 A1* | 6/2016 | Blum .................... F41C 33/029 |
| | | 348/372 |
| 2016/0344924 A1 | 11/2016 | Tsai |
| 2017/0108715 A1* | 4/2017 | Bauer .................... H04W 4/14 |
| 2017/0257595 A1 | 9/2017 | Newell et al. |
| 2018/0091729 A1* | 3/2018 | Hanover ................ G02C 11/10 |
| 2018/0234660 A1 | 8/2018 | Fitzgerald et al. |
| 2018/0338119 A1* | 11/2018 | Hoffman ............. H04L 65/4015 |

\* cited by examiner

CONTINUOUS VIDEO CAPTURE GLASSES

RELATED APPLICATION

This application claims the benefit of priority to U.S. Provisional Patent Application Ser. No. 62/638,820 for "Continuous Video Capture Glasses," filed Mar. 5, 2018.

FIELD OF THE INVENTION

The present invention pertains generally to video recording. More particularly, the present invention pertains to a glasses-mounted video recording apparatus. The present invention is particularly, but not exclusively, useful as a device for continuous video recording.

BACKGROUND OF THE INVENTION

In the 1980s, camcorders have brought video making capability within the reach of an ever-increasing number of consumers. Recording originally to videocassettes in an analog format, camcorders later acquired capabilities for digital video recording. With the changes in recording format came smaller sizes, lower prices, and improved video quality, resulting in increasing popularity of video production among consumers. The popularity of consumer video production has been further increased by the development of sharing and distribution channels, starting with television programs such as "America's Funniest Home Videos," and more recently video-sharing websites such as YouTube.

Meanwhile, the nature of consumer video production has changed—or rather broadened. Consumers are no longer limited to the use of dedicated camcorders; still cameras and mobile phones have acquired video recording capabilities and enjoy widespread consumer use. Moreover, specialized cameras, including action cameras such as those sold by GoPro, Inc., enjoy popularity among consumers desiring hands-free recording of their activities from a first-person perspective.

Most recently, wearable technology with video recording capability has received significant promotion in the marketplace, although its reception by consumers has been less than enthusiastic. The lack of success is due in part to the low battery capacity of such devices, which significantly limits the amount of video that can be taken without draining the battery.

In light of the above, it would be advantageous to provide a video recording device configured for convenient recording in a first-person perspective in situations in which an action camera is unnecessary or unwanted. It would be further advantageous to provide such a video recording device configured for hands-free recording. It would be further advantageous to provide such a device with sufficient battery life to record multiple hours of video between charges.

SUMMARY OF THE INVENTION

A set of glasses frames includes electronic components for video capture and is configured to continuously capture video in a twenty-second loop. On the frames is a capture button that, when pressed, causes the electronic circuitry to store forty seconds of video in non-transitory memory—that is, to save the twenty seconds of video prior to pressing the capture button along with the following twenty seconds of video.

The electronic circuitry in the frames also includes a Bluetooth radio and a Wi-Fi radio, enabling the frames to communicate with a mobile device, and more particularly to provide the saved twenty-second video clips to an app running on the mobile device. The app allows for storage of the video clips on the phone, editing of the video clips, upload of the video clips to the Internet, and configuring user-adjustable settings on the electronic circuitry of the glasses.

As seen in the above diagram, the glasses include a battery (or a pair of batteries, one on each arm of the frames) serving as a power source for the various components. A processor manages the operation of the various components. A camera, which may be composed of a charge-coupled device (CCD) and supporting circuitry, including a microphone, continuously captures video with at least 1080p resolution. Although ostensibly managed by the processor, the camera may write to the working memory using Direct Memory Access (DMA) to reduce the workload on the processor.

The storage in the video is laid out as follows: From device activation, media is written to a circular buffer storing h.264 data in the device's working memory. This buffer can hold up to 20 seconds worth of media before it overwrites itself with new media. When the user motions for the device to save the media, the buffer is resized to store an additional 20 seconds worth of media for a total buffer size of 40 seconds. This happens so that a continuous stream of media is saved from 20 seconds before and 20 seconds after media saving is initiated. Once media has filled the 40 second buffer, the device converts and saves the data as an mp4 file with a generated filename. After, the buffer is resized to resume capturing 20 seconds of media in a circular buffer. Data conversion, file storage, and resumed storage of media input in the 20 second buffer happen immediately in succession to ensure that the device is constantly recording and that no content is lost.

The capture button on the frames initiates a transfer of the previous twenty seconds of video from working memory—as well as the next twenty seconds being stored to the rest of the extended buffer—to the non-transitory memory. This is generally implemented by configuring the button to signal an interrupt to the processor when pressed, which is then handled by a software procedure to initiate the memory transfer. Additionally, at the time the capture button is pressed, the system allocates memory for an additional 20 seconds of media so that recording may continue while the transfer is taking place, and ultimately so that a total of 40 seconds of media is stored. Bluetooth and Wi-Fi radios further allow for communication with an external computing device, such as a mobile phone, running an app to store, edit, and upload the videos from the glasses and configure user-adjustable settings on the glasses.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION

Figure 1:
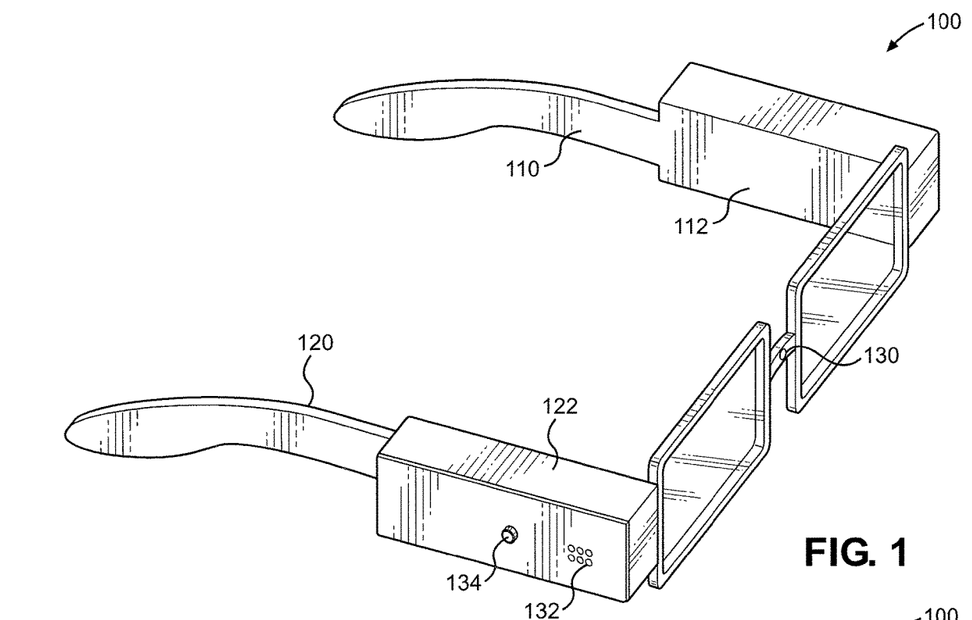
FIG. 1 is a perspective view of a preferred embodiment of continuous video capture glasses.

Referring initially to FIG. 1, a preferred embodiment of continuous video capture glasses is shown and generally designated 100. Glasses 100 comprise a left temple 110 having a left temple housing 112 and a right temple 120 having a right temple housing 122. An camera 130 with an image sensor 131 (not shown in FIG. 1) is shown mounted on the bridge of glasses 100, but in some embodiments is placed on the front of the left temple housing 112 (that is, the end of the temple housing nearest the wearer's eye), or the front of the right temple housing 122. In a preferred embodiment, image sensor 131 is an active pixel sensor ("APS"), though alternative embodiments it is a charge-coupled device ("CCD"). It will be apparent to one of skill in the art that other imaging devices may be used without departing from the scope and spirit of the invention. A microphone 132 is also present in preferred embodiments of glasses 100.

Glasses 100 continuously capture video from image sensor 131 and audio from microphone 132. When a wearer presses a button 134 on the glasses 100, the most recent twenty (20) seconds of captured video and the next twenty (20) seconds of captured video are stored in a file.

Figure 2:
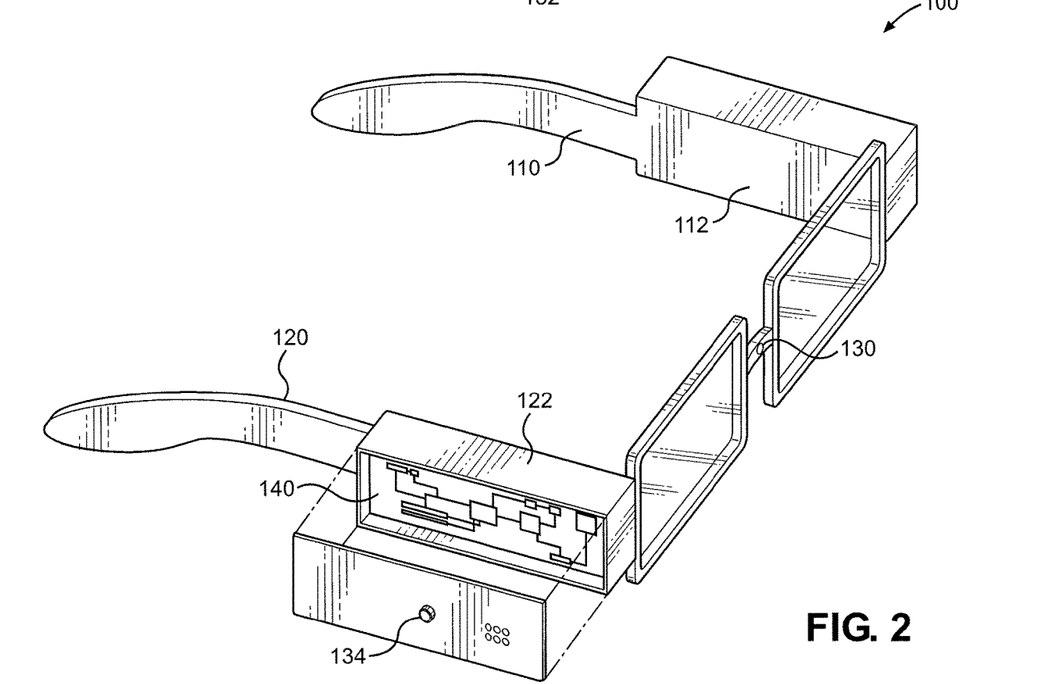
FIG. 2 is an exploded view of the continuous video capture glasses of FIG. 1.

Referring now to FIG. 2, the glasses 100 additionally comprise electronic circuitry 140 in order to capture and store the video from image sensor 131 and audio from microphone 132. Some major components of the electronic circuitry 140 are discussed in greater detail in connection with FIG. 4. The electronic circuitry 140, including batteries, and in some embodiments excepting the image sensor 131 and/or the microphone 132, is housed in left temple housing 112 and right temple housing 122. By including a housing for batteries and other electronic components on both left temple 110 and right temple 120, a greater amount of space is available for storage of electrical energy (that is, the batteries), allowing the glasses 100 to operate continuously, and, more particularly, to capture video continuously for a substantial amount of time: several hours in preferred embodiments.

Figure 3:
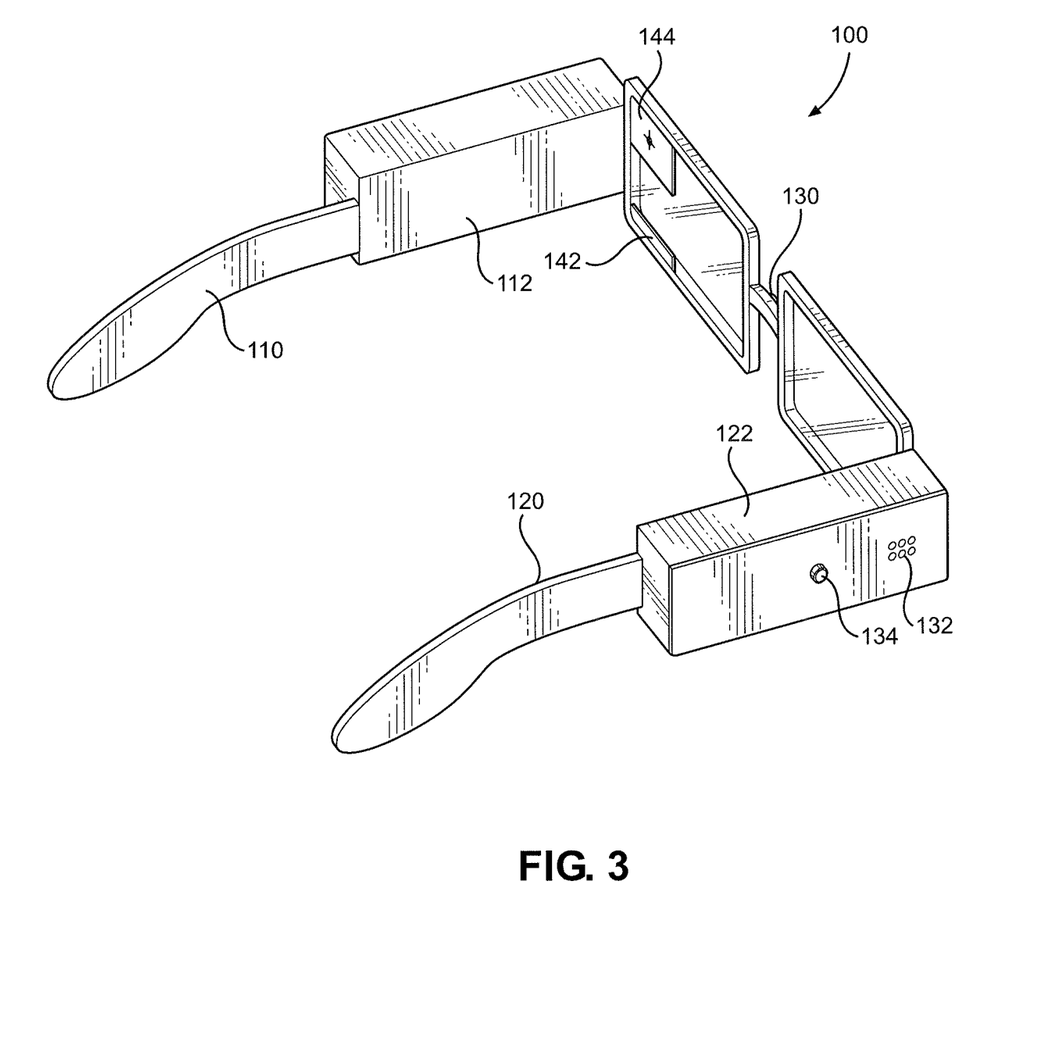
FIG. 3 is a perspective view of a preferred embodiment of continuous video capture glasses with eye-tracking apparatus.

Referring now to FIG. 3, eye-tracking technology has traditionally been confined primarily to research, especially in neuroscience and psychology research, safety-related research and engineering, and in marketing research funded by large commercial enterprises. As a result, an emphasis has been placed on precision and accuracy, and much of the available technology is not only expensive, but also requires specialized training to use. A unique aspect of a preferred embodiment of the present invention is the importation of eye-tracking technology into the field of consumer photography and video capture. More particularly, eye-tracking technology incorporated into a preferred embodiment of glasses 100 is used to automatically focus the camera 130 at an object being observed by a user.

Not every movement of the eye needs to be tracked, since it is desirable to focus the camera 130 only on objects upon which the eye fixates at least momentarily, rather than to continually refocus with every sudden jerk of the eye. Also, even a fairly rough estimate of eye position provides surprisingly good results, since generally the object to which attention is given is not extraordinarily small, thus there is a certain degree of flexibility in selecting the point of focus. As a result, the eye-tracking apparatus used can be relatively inexpensive, having a relatively low sampling rate and a relatively low resolution. For the same reasons, the need for calibration can be avoided for most users, although calibration routines are provided in a preferred embodiment for users that may desire greater accuracy. It is fully contemplated that the eye-tracking features may be implemented in combination with all the features of the other embodiments of glasses 100 described herein.

In a preferred embodiment, an eye-tracking apparatus includes an infrared light source 142 and a camera 144 mounted on the frame of glasses 100 around a lens, or a location where a lens would be located in a normal pair of glasses, as some embodiments of glasses 100 do not have lenses. It is sufficient to use a low-resolution camera 144, such as a camera that provides images of 1024×768, 800× 600, or even 640×480 pixels. Light from infrared light source 142 reflects from the cornea of a user. The corneal reflection and pupil are identified in a frame produced by camera 144 using pattern-recognition software; the pupil center is estimated, and a vector from the pupil center to the corneal reflection is calculated. This vector is used to estimate the direction and angle to which the user's eye is turned, and thus the approximate direction in which the user is looking.

Outdoors, reflections from sunlight may interfere with the detection of the corneal reflection, so the software falls back to estimating gaze direction based on the pupil center alone. This results in a small loss of accuracy, but is usually sufficiently accurate for use in focusing the camera 130. Some embodiments improve the accuracy of the fallback method by estimating, based on the shape and location of the eye in the captured frame, the point where the pupil would be when the user is gazing forward.

In an alternative embodiment, the infrared light source 142 is omitted entirely, and the above-described fallback calculations are the primary method for eye-tracking and selecting the point of focus for camera 130.

The eye-tracking apparatus may be on either lens or side of the glasses 100, and in at least one embodiment, an eye-tracking apparatus is on each side of the glasses 100. The availability of embodiments with eye-tracking apparatus on either side may allow the glasses 100 to be more useful to people with certain eye-related disabilities. The availability of embodiments with eye-tracking apparatus on both sides may also allow the glasses 100 to be more useful to people with certain eye-related disabilities, and further allow greater accuracy in the eye-tracking features of the glasses 100.

Figure 4:
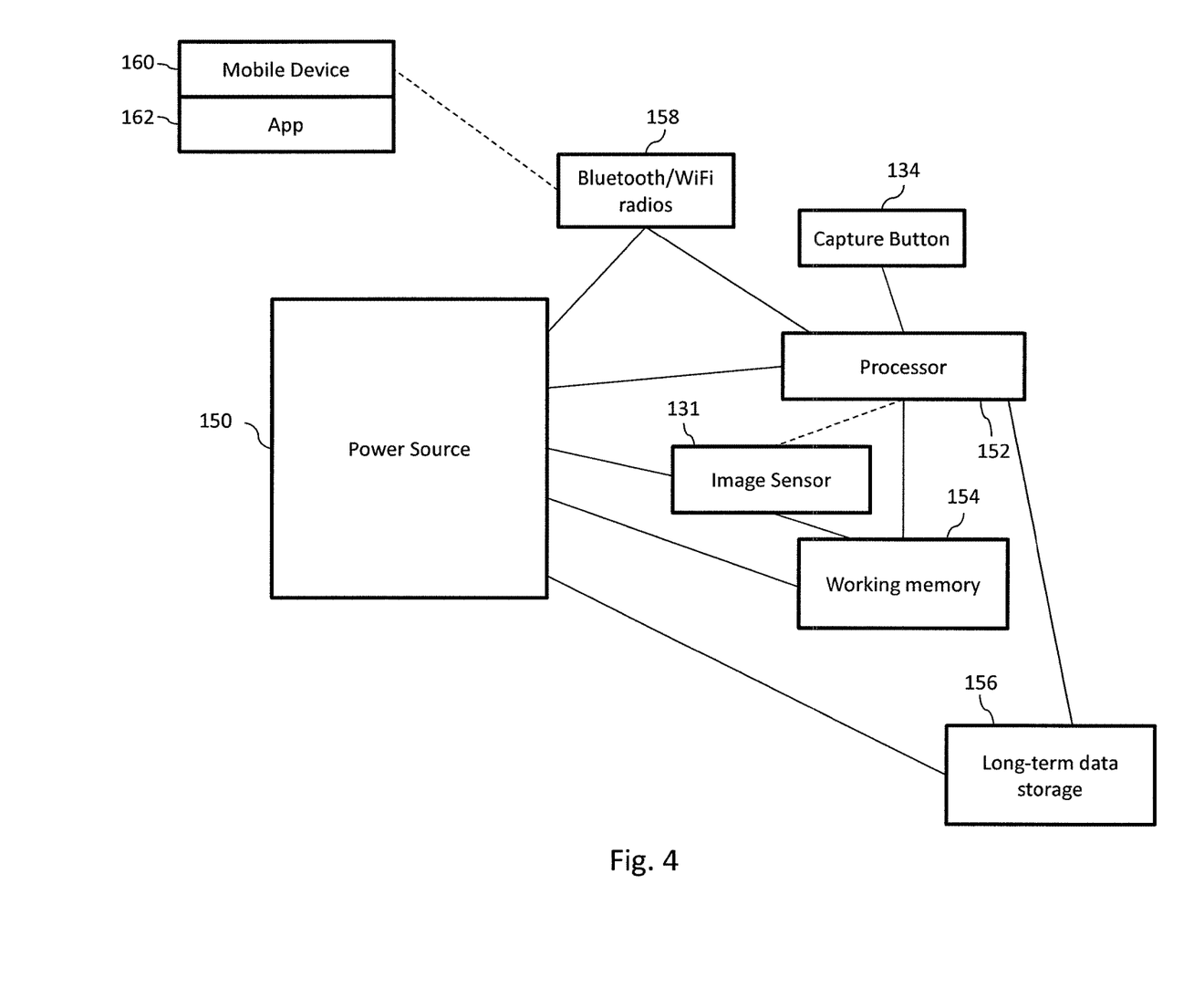
FIG. 4 is a diagram of various electronic components of the continuous video capture glasses of FIG. 1.

Referring now to FIG. 4, various electronic components of glasses 100 are shown. A power source 150, comprising batteries in a preferred embodiment, powers the various other electronic components. In a preferred embodiment, the power source 150 is capable of storing at least one-thousand (1000) mAh of energy, which allows for at least between seven (7) and ten (10) hours of recording time. In some preferred embodiments, power source 150 includes one or two user-removable and replaceable batteries, allowing a user to carry spare batteries for the glasses 100. A processor 152 runs software managing the operation of the glasses 100. Supporting the processor is non-transitory memory in the form of working memory 154, such as random-access memory (RAM), comprising one or more buffers for video storage. Working memory may also include read-only memory (ROM), in preferred embodiments in the form of electrically erasable programmable read-only memory (EE-PROM), containing instructions operated on by the processor 152 and causing it to execute processes to control the operation of glasses 100, including the processes described herein. Alternatively, in some embodiments some or all of the programs containing instructions operated on by the processor 152 are stored in storage 156 and may be loaded into working memory 154—usually RAM—as needed in order to execute the program instructions. Although processor 152 generally manages the capture of video and its storage in working memory 154, in some embodiments dedicated circuitry associated with the image sensor 131 and microphone 132 (not shown in FIG. 4) place the video and audio into the video storage buffers using Direct Memory Access ("DMA") in order to alleviate the burden on the processor 152. In other embodiments, software running on the processor 152 formats the captured video and audio using H.264 encoding for storage in the video storage buffers; some such embodiments use a processor 152 having multiple cores in order to enable the processor 152 to simultaneously undertake other tasks as necessary. Multiple processors 152 may also substitute effectively for the presence of multiple cores in a single processor 152.

A preferred embodiment uses one keyframe, or I-frame, every twenty-two (22) frames in encoding the video, which is stored at twenty-two (22) frames per second and 1080p resolution, for storage in the video storage buffers. These settings strike a balance allowing for reasonably good video quality to be stored in a reasonable amount of space. Nonetheless, other embodiments are adapted for differing needs related to the amount of video detail stored and the amount of memory available for buffer space, and include embodiments with more and less frequent I-frames, including embodiments with variable number of I-frames per second, embodiments with frame rates other than twenty-two frames per second (such as thirty frames per second and sixty frames per second), and embodiments with different resolutions (such as 720p, 1080i, and 4K).

When the capture button 134 is pressed, the processor 152 immediately allocates memory space for an additional twenty (20) seconds of video, into which the continued capture of video and audio is stored. Meanwhile, the video and audio from the previously allocated buffer is stored as a file in storage 156, which comprises non-transitory memory for long-term data storage, such as flash memory. The video and audio from the newly allocated memory space is also saved as the next twenty (20) seconds of video is captured, resulting in a forty-second stored video file. Since the saved video begins from the first available keyframe in the buffer, the runtime of the stored video may vary slightly, but will differ from forty seconds only by a negligible amount: The difference will be less than one second.

An external I/O component 158 allows the glasses 100 to communicate with an external device 160, such as a mobile device, running software 162, such as an app downloaded to a mobile device, for communicating with glasses 100. In preferred embodiments, external I/O component 158 includes at least one wireless radio, for example, one or both of a Bluetooth radio and a Wi-Fi radio. When a connection to an external device is active, once a video file has been stored in storage 156, it is transferred to the external device through external I/O component 158. In preferred embodiments, the external device will have software providing video editing and upload features, allowing the user to edit the transferred video and upload it to the Internet.

Figure 5:
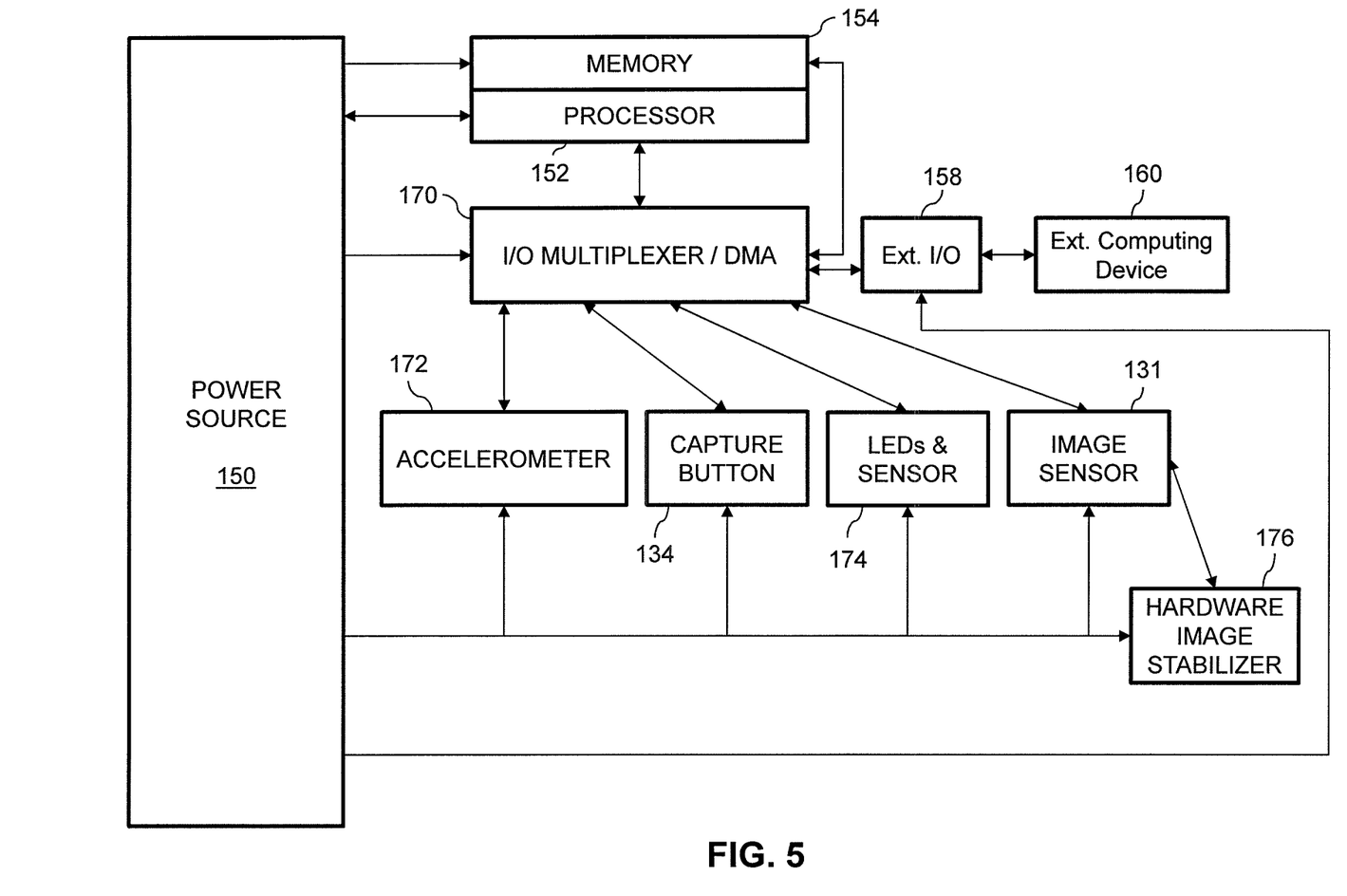
FIG. 5 is a diagram illustrating various components of preferred embodiments of the continuous video capture glasses of FIG. 1.

Referring now to FIG. 5, a conceptual diagram illustrates various components of preferred embodiments of glasses 100. FIG. 5 provides a somewhat different emphasis on the structure and certain features of preferred embodiments of glasses 100, therefore not all elements of FIG. 4 are shown in FIG. 5, nor are all elements of FIG. 5 shown in FIG. 4. Nonetheless, it should be understood that elements not shown are present in at least some preferred embodiments, and are only omitted for space and simplicity in presentation.

Illustrated in FIG. 5 is an I/O multiplexer 170, which may include DMA hardware to facilitate video storage with minimal burden on the processor 152, as discussed above. Multiplexer 170 allows the various devices integrated into glasses 100 to communicate with the processor 152. In some embodiments, a processor 152 may have several I/O pins and glasses 100 may have a limited number of devices that need to communicate with processor 152; in some such embodiments the devices simply communicate through the I/O pins on the processor 152, and multiplexer 170 is not present.

An accelerometer 172 is present in some preferred embodiments of glasses 100, and is used to implement features such as automatic saving of video and digital image stabilization. In a preferred embodiment, glasses 100 can be placed into a "dash cam mode" in which the previous twenty seconds of video and the following twenty seconds of video are stored when a sudden acceleration is detected via the accelerometer 172, as if the capture button 134 had been pressed. A sudden acceleration is a measurement by accelerometer 172 above a predetermined magnitude in a predetermined axis or axes, based on parameters programmed into glasses 100.

A light 174 on left temple 110, right temple 120, or both, illuminates from back to front indicating that video capture is in progress. As depicted in FIG. 5, light 174 is used, in a preferred embodiment, with a light sensor in order to dynamically adjust the light 174 brightness based on the ambient light. In a preferred embodiment, the brightness of the light 174 is lowered in darker environments, in which a particular light source is generally perceived more easily. The corollary is that light 174 would be brighter in a well-lit area, retaining its visibility to an observer. In a preferred embodiment, the light 174 moves or extends corresponding to the placement of video into working memory 154, as further discussed below. In a preferred embodiment, light 174 is made of a row of light-emitting diodes (LEDs). Light 174 in some embodiments is on temple housing 112 or 122 rather than directly on the temple 110 or 120.

An image stabilizer 176 is present in some preferred embodiments. A preferred embodiment of image stabilizer 176 is a sensor-shift image stabilizer that moves the image sensor 131 as necessary to compensate for shaking of the glasses 100. In some embodiments, image stabilization may be performed by processor 152 through cropping the frames received by the image sensor 131, a digital signal processing (DSP) program, or both. Digital image stabilization through cropping or through a DSP program and hardware image stabilization through image stabilizer 176 are not mutually exclusive, and some embodiments use both forms of image stabilization.

Figure 6:
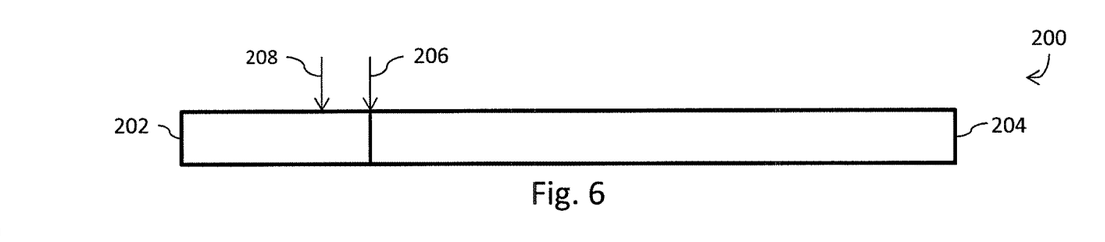
FIG. 6 is a diagram of the memory layout for the video recording buffer of the continuous video capture glasses of FIG. 1.

Referring now to FIG. 6, the layout of a circular buffer 200 is shown. The length of buffer 200 is sufficient to hold at least twenty (20) seconds of video data, including audio in preferred embodiments. Other embodiments may store audio in a separate buffer 200. Buffer 200 has a beginning address 202 in memory, an ending address 204, a data end address 206, and a data start address 208. If beginning address 202 is tracked with a pointer, ending address 204 may be determined by either a pointer, or a length or offset from beginning address 202; data end address 206 and data start address 208 can likewise be determined by either a pointer or an offset from beginning address 202. Moreover, in embodiments in which the video and audio are captured uncompressed at a fixed bitrate, a separate data start address 208 need not be tracked, since after twenty (20) seconds of operation of the glasses 100, it will be the same as data end address 206. However, in preferred embodiments compression is used, and the portion of the buffer 200 used for twenty seconds worth of storage varies. When the portion of the buffer 200 used varies, data end address 206 and data start address 208 will generally not be the same.

The pointer for data end address 206, or data start address 208, or both are used for determining the portion or portions of light 174 that are lit up. Light 174 is thus lit up to correspond with the data being placed into buffer 200.

During use of the glasses 100, data end address 206 is continuously adjusted toward the ending address 204 of the buffer 200 as data are added to the buffer 200. Once data end address 206 reaches the ending address 204, it is updated to point to the beginning address 202 of the buffer 200, and continues onward toward ending address 204, repeating the cycle throughout the period of use of the glasses 100. Likewise, data start address 208 undergoes a similar progression upon reaching twenty (20) seconds of operation of the glasses 100.

Figure 7:
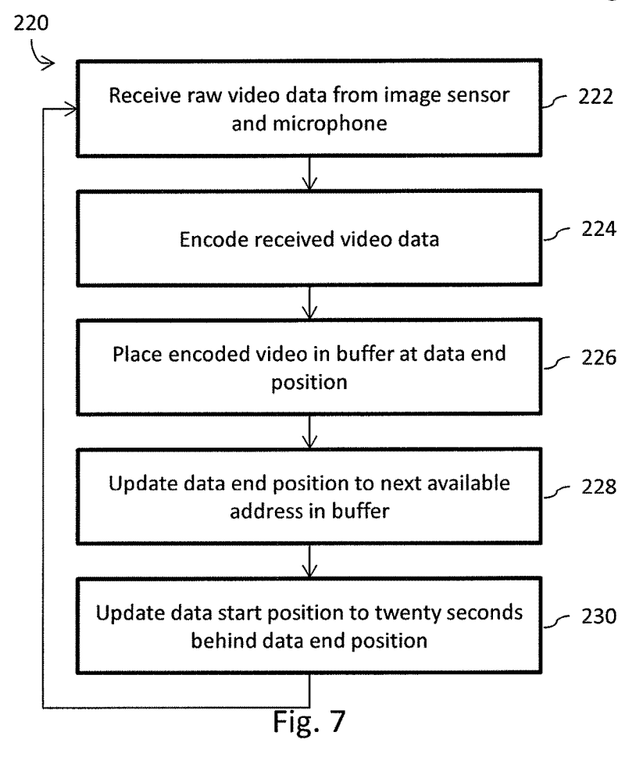
FIG. 7 is a flowchart describing the process of continuous video recording as performed by the continuous video capture glasses of FIG. 1.

Referring now to FIG. 7, the principal steps in the process of continuous video capture as performed by glasses 100 are shown and generally designated 220. Process 220 is generally performed by processor 152 in conjunction with other components of the glasses 100, but, as mentioned above, in some embodiments some or all of the steps are performed by separate circuits attached to the image sensor 131 and the microphone 132 through Direct Memory Access.

In step 222, raw video and audio data are collected from the image sensor 131 and the microphone 132. In step 224, the raw video and audio data are encoded; in a preferred embodiment, the data are encoded in a compressed format, using the H.264 format. In certain embodiments using DMA, a "raw" or uncompressed format is used for simplicity. In step 226, the encoded data are placed in a buffer 200 (or, depending on the format, a set of buffers 200) beginning at the data end address 206. Then, in step 228, the data end address is incremented to point to the next available address in the buffer 200. Since a circular buffer 200 is used, the presence of old data ready to be overwritten does not prevent an address from being the next available address. The data start address 208 is also updated, in step 230, so that it falls at the portion of video data corresponding to twenty (20) seconds prior to the portion of video just added to the buffer in step 226. The process 220 is then repeated, beginning again at step 222 with the next segment of video data. Process 220 thus runs in a loop while the glasses 100 are in operation.

Figure 8:
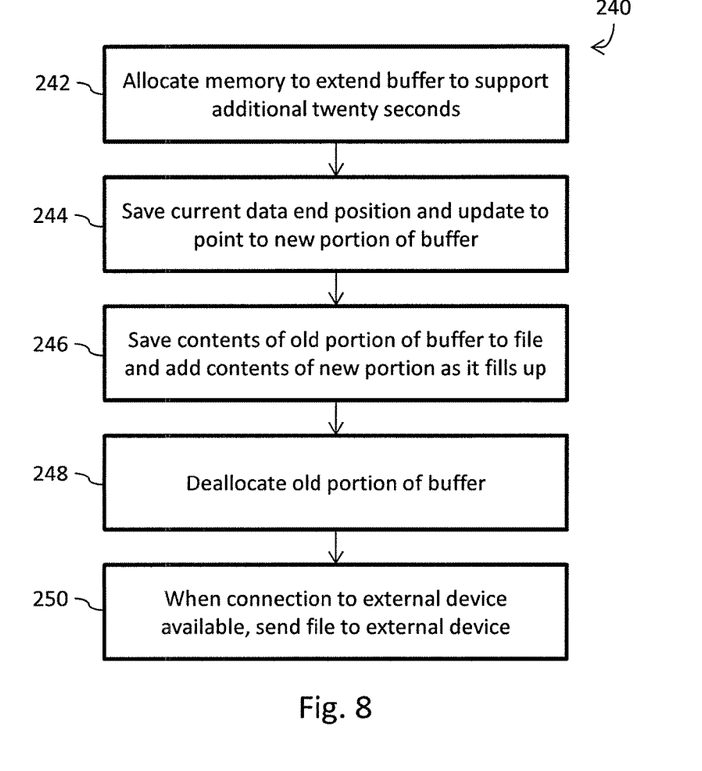
FIG. 8 is a flowchart describing the process initiated when a user presses the capture button on the continuous video capture glasses of FIG. 1.

Referring now to FIG. 8 the principal steps in the process of storing captured video are shown and generally designated 240. Process 240 is initiated when the wearer presses button 134, and, in some preferred embodiments, through other means such as sudden acceleration, or through a signal from software 162 generated at the user's request. For example, A mobile device 160 may be a smartwatch (usually in addition to a mobile phone), and software 162 running on the smartwatch provides a user interface feature engageable by the user to signal glasses 100 to begin process 240. Once button 134 is pressed or process 240 is initiated in another way, process 240 begins with step 242 of allocating memory to extend the buffer 200 to hold an additional twenty (20) seconds of video. Then, in step 244, the current data end address 206 is saved (for example, in a predetermined register of processor 152) and the data end address 206 is updated to point to the new portion of the buffer 200. A copy of the data start address 208 is also saved at this time, thus marking the boundaries of a twenty (20) second span of video for storage. The update of data end address 206 causes process 220 to store newly captured video in the newly allocated portion of the buffer 200, thus avoiding loss of any video while storing the twenty (20) seconds prior to the pressing of button 134.

In step 246, the twenty (20) seconds of video between data start address 208 and data end address 206, as calculated using the old boundaries of the buffer 200, are saved to a file in storage 156. As the new portion of the buffer fills up, the next twenty (20) seconds of video is also saved to the file in storage 156. Then, in step 248, the old portion of the buffer 200 is deallocated. The deallocation may be performed gradually so that twenty (20) seconds of video is always maintained, or may be scheduled to occur twenty (20) seconds after the allocation of the new portion of the buffer 200, or even forty (40) seconds after the allocation of the new portion of the buffer 200 when it is desirable to wait until the forty-second video file is saved to storage 156. When a connection to an external device, such as mobile device 160, is available, step 250 is performed, involving the transfer of the stored file to the external device.

Figure 9:
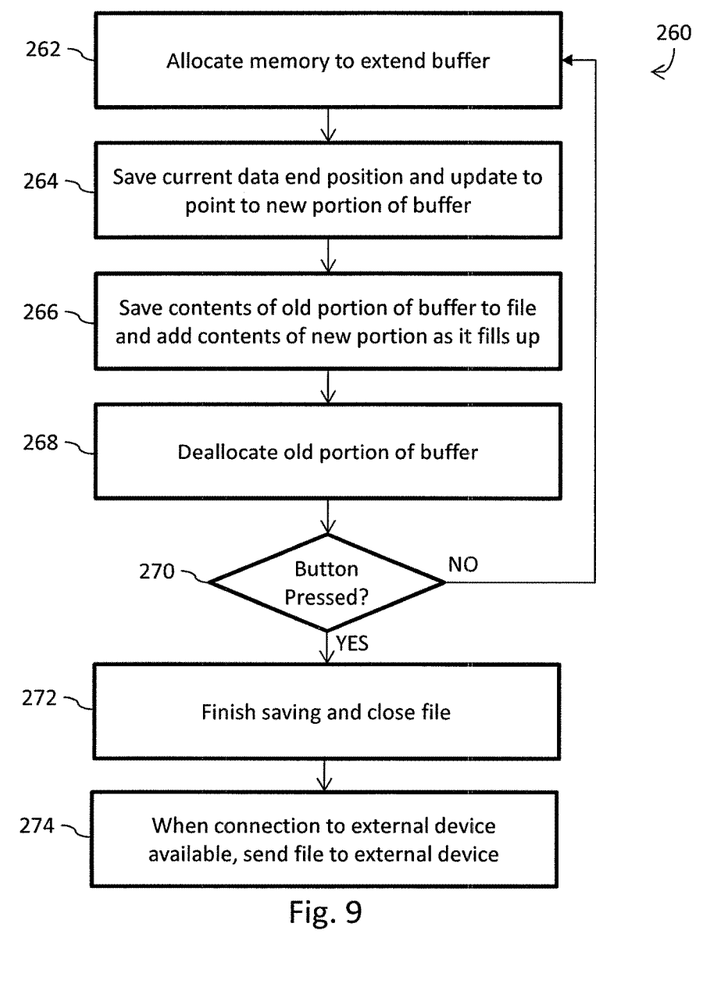
FIG. 9 is a flowchart describing the process initiated when a user presses the capture button twice on the continuous video capture glasses of FIG. 1.

Referring now to FIG. 9, some preferred embodiments of the glasses 100 allow a user to double-press button 134, or press button 134 a second time during the twenty (20) second period before step 248 of process 240 in order to continue saving video until the user presses button 134 a third time.

The second press of button 134 causes the glasses 100 to loop the initial steps of process 240 as depicted by process 260, allocating additional memory for the buffer in step 262, which may include greater amounts of memory than in step 242 in order to avoid frequent allocations of additional memory, updating the relevant pointers in step 264, saving the buffer contents to a file in step 266, and deallocating portions of the buffer which are no longer needed in step 268, all in a similar fashion to the corresponding steps of process 240. These operations are continued until the button is pressed in step 270, at which point any unsaved contents of the buffer are placed into the file and the file is closed in step 272. As in process 240, when a connection to an external device, such as mobile device 160, is available, step 274—analogous to step 250—is performed, involving the transfer of the stored file to the external device. Step 274 in process 260 (or step 250 in process 240) may be performed simultaneously with other steps, for example, if a connection to an external device is available at the beginning or early on in process 260 or 240.

While there have been shown what are presently considered to be preferred embodiments of the present invention, it will be apparent to those skilled in the art that various changes and modifications can be made herein without departing from the scope and spirit of the invention.

What is claimed is:

1. A continuous video capture apparatus, comprising:
   glasses frames having:
      a first temple having a first temple housing, and
      a second temple having a second temple housing;
   a power source located in the first temple housing;
   a second power source located in the second temple housing;
   a video capture camera;
   a microphone; and
   electronic circuitry located in the second temple housing, the electronic circuitry comprising:
      a memory,
      a processor,
      a wireless radio, and
      a capture button,
   wherein the electronic circuitry is configured to continuously capture video from the video capture camera and microphone and maintain a most recent twenty seconds of video in the memory, and
   wherein the capture button is engageable by a user to cause the electronic circuitry to send the most recent twenty seconds of video and a subsequent twenty seconds of video to an external device.

2. The continuous video capture apparatus of claim 1, wherein the power source comprises a user-removable battery.

3. The continuous video capture apparatus of claim 1, wherein the electronic circuitry further comprises an accelerometer.

4. The continuous video capture apparatus of claim 3, wherein the electronic circuitry is configured to send the most recent twenty seconds of video and a subsequent twenty seconds of video to the external device upon detection of a sudden acceleration by the accelerometer.

5. A continuous video capture apparatus, comprising:
   glasses frames having:
      a first temple having a first temple housing, and
      a second temple having a second temple housing;
   a power source located in the first temple housing;
   a video capture camera;
   a microphone;
   an eye-tracking camera mounted on the glasses frames, wherein the electronic circuitry is configured to acquire images from the eye-tracking camera, estimate a gaze direction of the user, and focus the video capture camera on an object in the gaze direction; and
   electronic circuitry located in the second temple housing, the electronic circuitry comprising:
      a memory,
      a processor,
      a wireless radio, and
      a capture button,
   wherein the electronic circuitry is configured to continuously capture video from the video capture camera and microphone and maintain a most recent twenty seconds of video in the memory, and
   wherein the capture button is engagable by a user to cause the electronic circuitry to send the most recent twenty seconds of video and a subsequent twenty seconds of video to an external device.

6. The continuous video capture apparatus of claim 5, further comprising an infrared light source mounted on the glasses frames, the infrared light source configured to generate a corneal reflection in the images from the eye-tracking camera, wherein the electronic circuitry is configured to estimate the gaze direction based on a pupil center and a location of the corneal reflection.

7. A continuous video capture apparatus, comprising:
   glasses frames having:
      a first temple having a first temple housing, and
      a second temple having a second temple housing;
   a power source located in the first temple housing;
   a video capture camera;
   a microphone; and
   electronic circuitry located in the second temple housing, the electronic circuitry comprising:
      a memory,
      a processor,
      a wireless radio, and
      a capture button,
   wherein the electronic circuitry is configured to continuously capture video from the video capture camera and microphone and maintain a most recent twenty seconds of video in the memory, and
   wherein the capture button is engageable by a user to cause the electronic circuitry to send the most recent twenty seconds of video and a subsequent twenty seconds of video to an external device; and
   wherein the electronic circuitry is configured to send the most recent twenty seconds of video and a subsequent twenty seconds of video to the external device upon receipt of a command from a second external device.

8. The continuous video capture apparatus of claim 7, wherein the second external device is a smartwatch.

* * * * *